US010932426B2

(12) United States Patent
Christensen et al.

(10) Patent No.: US 10,932,426 B2
(45) Date of Patent: Mar. 2, 2021

(54) BOUQUET OF CUT FLOWERS

(71) Applicant: KNUD JEPSEN A/S, Hinnerup (DK)

(72) Inventors: Ellen Margrethe Skovsgaard Christensen, Hinnerup (DK); Kai Lønne Nielsen, Hinnerup (DK)

(73) Assignee: KNUD JEPSEN A/S, Hinnerup (DK)

( * ) Notice: Subject to any disclaimer, the term of this patent is extended or adjusted under 35 U.S.C. 154(b) by 0 days.

(21) Appl. No.: 15/114,281

(22) PCT Filed: Jan. 26, 2015

(86) PCT No.: PCT/EP2015/051495
§ 371 (c)(1),
(2) Date: Jul. 26, 2016

(87) PCT Pub. No.: WO2015/110635
PCT Pub. Date: Jul. 30, 2015

(65) Prior Publication Data
US 2017/0172085 A1  Jun. 22, 2017

(30) Foreign Application Priority Data

Jan. 27, 2014  (NL) .................................... 2012150

(51) Int. Cl.
*A01H 6/32* (2018.01)
*A01H 5/02* (2018.01)
*A01N 3/02* (2006.01)
*A01H 5/04* (2018.01)

(52) U.S. Cl.
CPC ............... *A01H 6/324* (2018.05); *A01H 5/02* (2013.01); *A01H 5/04* (2013.01); *A01H 6/32* (2018.05); *A01N 3/02* (2013.01)

(58) Field of Classification Search
CPC ..................................................... A01H 6/324
USPC ................................................. Plt./335–341
See application file for complete search history.

(56) References Cited

U.S. PATENT DOCUMENTS

PP12,299 P2 * 12/2001 Jepsen .................. A01H 5/0266
Plt./338
PP18,074 P2 * 8/2007 Jepsen .................. A01H 5/0266
Plt./340

FOREIGN PATENT DOCUMENTS

EP  1671536  6/2006

OTHER PUBLICATIONS

Shoen Royal Flower Classroom Blog, Jan. 31, 2013 Arangement of Royal Flowers with Flower Crumbs, web page at takuhou-blog.jugem.jp/?month=201301.*
Leszczynska-Borys et al 2002 Revista Chapingo Serie Horticultura 8(1): 119-123.*
Izumikawa et al 2007 Acta Horticulturae vol. 743, Proceedings of the XXnd International Eucarpia Symposium (Sect. Ornamentals) on Breeding for Beauty (vol. II), Eds. A. Mercuri and T. Schiva.*
Koene, Robert "Kalanchoe as cut flower in wedding bouquet" Jul. 18, 2008, Retrieved from the internet: URL: youtube.com/watch?v=lae09_Is0A [retrived on Aug. 11, 2014], 1 page.
Hooftman, J "Gek op Kalanchoe", Bloem En Blad, No. 8, Aug. 1, 2012, pp. 10-18.
Anonymous: "Danish kalanchoe breeder steps into cut flower industry" Jan. 15, 2014, Retrieved from the internet URL: newplantsandflowers.com/danish-kalanchoe-breeder-steps-into-cut-flower-industry/ retrieved on Aug. 12, 2014], 2 pages.
Bjarke, L "Ethylene resistant Kalanchoes from Denmark", Flora Culture International, Mar. 1, 2012, pp. 16-17, Retrived on from the internet: floraculture.eu/digizine/march2012_2/magazine.html [retrieved on Aug. 12, 2014].
Leszczynska-Borys H. et al. "Bryophyllum pinnatum Kurz.—A new cut flower species. I. Aesthetic Value", Revista Chapingo Serie Horticultura, vol. 8, Dec. 8, 2002, pp. 119-123.
Blog of Takuhou, "Arrangement of royal flowers with flower crumbs" royal flower arrangement school, article dated Jan. 31, 2013, searched on Jan. 23, 2017, URL: takuhou-blog.jugem.jp/?month=201301, 7 pages.
Hana-no-Saburo, "Autumn's Flower arrangement in autumn", article dated Aug. 23, 2013, searched on Jan. 23, 2017, URL: blogs.yahoo.co.jp/nobu04151117/11393297.html, 5 pages.
Hare-tokidoki-syumi-no-engei, Kalanchoe-no-sashiki, "Sunny and sometimes hobby gardening", article dated Jun. 6, 2011, searched on Jan. 23, 2017, URL: tokidoki-engei.com/blog-entry-370.html, 11 pages.
Hooftman, J "Gek op Kalanchoe", Bloem En Blad, 8:10-19 (2012).
Taspo, As cut flowers: Kalanchoe in new clothing, downloaded on Oct. 7, 2019, from https://taspo.de/gruene-branche/als-schnittblumen-kalanchoe-in-neuem-gewand/ (Mar. 2, 2014).

* cited by examiner

*Primary Examiner* — David H Kruse
(74) *Attorney, Agent, or Firm* — Browdyand Neimark, PLLC (57) ABSTRACT

Described is a flower bouquet conferring extended freshness to an aqueous nutrient medium for keeping cut flowers, as well as a method to confer a prolonged longevity to one or more cut flowers, comprising the step of allowing one or more cut flowers, with the cut surface of the stem thereof, to be in contact with the said aqueous nutrient medium.

25 Claims, 7 Drawing Sheets

BOUQUET OF CUT FLOWERS

The invention relates to a bouquet of cut flowers capable of conferring elongated freshness to an aqueous nutrient medium for cut flowers, to a method for conferring elongated freshness to an aqueous nutrient medium for cut flowers, to the use of one or more cut flowers for prolonging the longevity of one or more cut flowers, and to a method for prolonging the longevity of one or more cut flowers.

Both florist and customers usually keep bouquets of cut flowers in an aqueous liquid nutrient medium, such as tap water or water enriched with plant nutrients. The flowers can be kept e.g. in a vase or a bucket, or any other suitable container that holds aqueous nutrient medium and allows the stems of the cut flowers to be in contact with the aqueous medium, in particular allowing the cutting edge of the stems to be submersed in the aqueous nutrient medium, and thus allowing the cut flowers to take up water and nutrients from the medium.

However, a well-known problem of cut flowers is the relatively short longevity. This phenomenon starts at the moment the stem of the flowers are cut, and put in the liquid nutrient medium. The medium start fouling within a relatively short period of time, resulting in early decay of the cut flowers. For florists, this problem is serious, as a significant portion of the flowers wither in the period that the flowers are offered for sale. Also customers are facing this problem, as many cut flowers only hold for a limited number of days. Both the florist and the customer would benefit significantly from elongation of the longevity of cut flowers.

The present inventors have now very surprisingly found that the aqueous nutrient medium has an elongated freshness, i.e. is less susceptible to fouling when the bouquet comprises one or more cut flowers belonging to the genus *Kalanchoe*. It was noticed that the aqueous nutrient medium, such as tap water or water enriched with plant nutrients, remained fresh and odor free for as long as the stem of the cut flowers belonging to the genus *Kalanchoe* were submerged in the aqueous nutrient medium (up to 8 weeks).

Therefore, the invention relates to a bouquet of cut flowers capable of conferring elongated freshness to an aqueous nutrient medium for cut flowers by contact of the cut surface of the stems of the said cut flowers with the said aqueous nutrient medium, said bouquet comprising one or more cut flowers belonging to the genus *Kalanchoe* having a stem length of at least 35 cm.

Interestingly, it was believed that succulents such as *Kalanchoe* were not to be suitable as cut flowers. Natural habitats for succulents are very dry areas. Succulents therefor do not need much water, and in contrast, succulent tend to rather wilt and die when too much water is given. When cut flowers are in continuous contact with an aqueous nutrient medium, the said flowers are saturated with the medium. Such saturation would be detrimental for succulents grown in soil, or special growing medium used for potted plants. When used as cut flowers at all, succulents are generally kept dry, i.e. without being in contact with an aqueous nutrient medium. Plants of the genus *Kalanchoe* are succulents. As a potted plant, care should indeed be taken not to water *Kalanchoe* too much, resulting in wilting and eventual death of the plant, in particular in winter when the days become short. Nevertheless, cut flowers of the genus *Kalanchoe* are recently described, indeed to be kept dry, see e.g. www.newplantsandflowers.com/cut-flower-kalanchoes-that-can-stay-weeks-without-water/. Accordingly, *Kalanochoe* has been used in wedding bouquets, see e.g. www.youtube.com/watch?v=Iae09_1s04A. Such bouquets are indeed not intended to be kept in a liquid aqueous nutrient medium. In contrast, such a bouquet is intended to be carried by the bride during her wedding day, without any contact with aqueous nutrient medium.

Although some florists have started to use *Kalanchoe* in bouquets. Hooftman (Bloem en Blad nr 8, 2012, pp. 10-18) describes the problem of incorporating hitherto available *Kalanchoe* in large bouquets, as such *Kalanchoe* s were highly branched and relatively small, having a stem of about 20 cm. Indeed, the said *Kalanchoe* were used to produce relatively small bouquets wherein the flower of the said *Kalanchoe* was put on a wire. When such a bouquet was put in contact with a liquid nutrient medium, said wired *Kalanchoe* was kept above the said medium, i.e. not in contact therewith, see e.g. the "take-away bouquet"("meeneemboeketje" on page 12 of Hooftman, supra). It was indicated that after the bouquet was finished, the *Kalanchoe* flower could be kept longer by separating it from the finished flowers, cutting the flower again, resulting in a substantially stemless flower, and putting it in water separately. A similar proposal was made by the flower arrangement "impulse gift" ("impulscadeautje", page 13 of Hooftman, supra), where a single flower of the *Kalanchoe* 'variety lea' (CPVO 2005/1650) with a short stem of less than 10 cm. is arranged in a small flower assembly in a drinking glass. This variety is bred and selected for compactness, to be used as a potted plant for its compactness and excessive branching in the lower part of the stem.

The term "bouquet" intends to mean a collection of a plurality of cut flowers, the flowers preferably having a stem length of at least 35 cm, more preferably of at least 45 cm, or at least 50 cm. The cut flowers are intended to be arranged in a vase, capable to receive and hold cut flowers having a stem length of at least 35 cm. by the customer. In a preferred embodiment, a bouquet is also defined as a plurality of cut flowers having a stem length of at least 35 cm, the cut flowers being displayed or offered for sale, hold together by a foil wrap (e.g. of plastic or paper) and/or by a binders, holding the stems of the flowers of the bouquet together. A bouquet preferably comprises 3 or more cut flowers with a stem length of at least 35 cm, more preferably 5 or more cut flowers or even 7, 8 or 10 or more such cut flowers.

Accordingly, the "impulse gift" as described by Hooftman, supra cannot be regarded as a bouquet. This flower arrangement only comprises a short stemmed *Kalanchoe* in combination with a *Gerbera*, presented for sale in a small drinking glass, i.e. not a bouquet. Furthermore, it was not observed by Hooftman that *Kalanchoe* was capable of conferring elongated freshness to the aqueous nutrient medium, resulting in prolonged longevity of cut flowers, arranged in a bouquet. Indeed, in such small arrangement, such fouling of the aqueous medium is very much less pronounced and appeared to have remained unnoticed.

Cut flowers belonging to the genus *Kalanchoe* can very well be kept in an aqueous nutrient medium, such as tap water, resulting even in a prolonged longevity as compared to when kept in the absence of an aqueous nutrient medium. Even more surprisingly, cut flowers belonging to the genus *Kalanchoe* confer elongated freshness to an aqueous nutrient medium for keeping cut flowers, even in the presence of other cut flowers. The medium stays clearer for a longer period. Such medium with elongated freshness surprisingly confers, to cut flowers kept therein, i.e. the cut surfaces of the stem thereof being submerged in the said nutrient medium, a prolonged longevity. Therefore, cut flowers belonging to the genus *Kalanchoe* have the ability to confer, not only to themselves, but also to other cut flowers, a prolonged longevity by allowing the cut surface of the stem of said *Kalanchoe* and, if desired, of such other cut flowers, to be in contact with the aqueous nutrient medium. The term 'aqueous nutrient medium' is meant to encompass all known media, intended for keeping cut flowers by contacting the cut stem of the said cut flowers with the said media. In particular, such media are liquid, such as tap water, optionally further enriched with nutrients as known in the art (such as marketed by Chrysal, Naarden, Netherlands). However, the aqueous media can also be in the form of a gel, or be held in another matrix such as (artificial) cotton wool or Oasis® Floral Foam (Kent, Ohio, USA), soaked with liquid nutrient medium.

It is surprisingly observed that cut flowers of the genus *Kalanchoe*, when, against all prejudices, are kept in an aqueous nutrient medium, said medium has an extended freshness, and tends to foul significantly later in time as compared to aqueous nutrient media wherein other cut flowers are kept, in the absence of *Kalanchoe*. Furthermore, the cut flowers belonging to the genus *Kalanchoe* have a better performance when kept in an aqueous nutrient medium as compared to keeping under dry conditions as prescribed in the art.

Without the intention to be bound by any explanation, it is believed that cut flowers of the genus *Kalanchoe* have an hitherto unnoticed antiseptic effect on the medium wherein they are kept, and may to this end comprise one or more substances that are excreted in the aqueous nutrient medium, which one or more substances are believed to be taken up by the other cut plants, as a result of which these plants obtain the ability to live longer and to wither far later than compared to the situation without a cut flower of the genus *Kalanchoe* being, or having been in contact with the aqueous nutrient medium wherein the said cut flower is held. It is therefore advantageous not to change the aqueous nutrient medium, in which the basal parts are submerged in order to maintain as high concentration as possible of the excreted substances from cut flowers belonging to the *Kalanchoe* genus, suppressing undesired microbial activity.

Larger *Kalanchoe* s do not only contribute to the attractive appearance of the bouquet, but it has also been found that the freshness of the liquid medium is elongated even more if the bouquet comprises larger *Kalanchoe* s. Therefore, in a preferred embodiment the cut flowers belonging to the genus *Kalanchoe* in the bouquet have a stem length of at least 45 cm, more preferably of at least 50 cm, and may even have a stem length of up to 60 cm or more. The stem length of the cut flower herein is defined by the length as measured from the cut surface of the stem to the node that is most remote from the said cut surface. In particular, not only the *Kalanchoe* present in the bouquet but the plurality and preferably all of the cut flowers of the bouquet have such a length.

In a very attractive embodiment, the cut flowers belonging to the genus *Kalanchoe* are free of branches that originate from the lower quarter of the cut flower. This means that in case a cut flower has a stem length of 40 cm, said flower is free of branches over the lowest 10 cm of the said stem. By being free of branches, such *Kalanchoe* is very suitable to be incorporated in a bouquet. To this end, it is even more preferable for the *Kalanchoe*, to be free of branches that originate from the lower third of the stem of the cut flower, even more preferably from the lower half thereof.

In particular, the cut flowers belonging to the genus *Kalanchoe* in the bouquet are not and have not been subjected to removal of branches before being incorporated in the bouquet. Although it is possible to use *Kalanchoe* varieties that have branches in the lower half thereof, which branches are then preferably been cut away by hand, it is highly preferred to use *Kalanchoe* varieties that do not or significantly not have branches as indicated above, so that there is no necessity to cut away any branches. The present inventors have been able to provide *Kalanchoe* varieties that fulfill such qualities, which will be discussed in more detail below.

In another attractive embodiment, the cut flowers belonging to the genus *Kalanchoe* in the bouquet are free of stems that reach not further than below the upper third, preferably the upper quarter of the stem.

Examples of suitable species of the genus *Kalanchoe* or incorporation in a bouquet are *K. ambolensis, K. aromatica, K. blossfeldiana, K. campanulata, K. citrina, K. coccinea, K. crundallii, K. daigremontiana, K. decumbens, K. dixoniana, K. faustii, K. fedtschenkoi, K. figueredoi, K. flammea, K. gastonis-bonnieri, K. glaucescens, K. gracilipes, K. grandiflora, K. guignardii, K. humilis, K. jongmansii, K. laciniata, K. latisepela, K. laxiflora, K. lobata, K. longiflora, K. manginii, K. marmorata, K. nyikae, K. obtuse, K. paniculata, K. pinnata, K. porphyrocalyx, K. prittwitzii, K. pubescens, K. pumila, K. rauhii, K. rotundifolia, K. scapigera, K. schumacherii, K. spathulata, K. streptantha, K. synsepala, K. tomentosa, K. thyrsiflora, K. tubiflora* and *K. uniflora*.

Preferred *Kalanchoe* varieties are double type, i.e. have more than four petals per flower, preferably more than 10, 20, 30, 35, 40 petals per flower.

Even more preferred are interspecific hybrids of *Kalanchoe* and progeny thereof, as e.g. disclosed in EP1671536, in particular those of double type and having the branching characteristics and lengths as described above.

In a particular embodiment, the interspecific hybrids originate from but a not limited to, a crossing with *Kalanchoe laciniata*. Interspecific hybrids originating from *Kalanchoe laciniata* also encompass any progeny thereof, i.e. obtained by further crossing and selection. Such interspecific hybrids have excellent flowering and varieties that have the envisaged stem length can conveniently be selected. As the first step in making new *Kalanchoe* interspecific hybrid of the instant invention, a fertile *Kalanchoe* plant selection is crossed with a fertile *Kalanchoe* selection from another species or a fertile *Kalanchoe* interspecific hybrid. Crossings are made by transferring fertile pollen from the pollen donor (♂) to the pollen receiver (♀). After seed maturation and seed harvest, the seeds are germinated. Seedlings are transferred to a suitable growing medium and three to six weeks after transplanting flowering is induced by short day treatment (day length 10 hours and 14 hours uninterrupted night). After flowering is induced, progeny are screened for required phenotypes, e.g. plant height, branching habit, stem strength, flower size, flower color, petal number as well as ethylene sensitivity and flower longevity. Large numbers of progeny may have to be screened to identify hybrids that meet the trait requirements. The hybrid progeny plant with desirable phenotypic characteristics is propagated asexually by conventional methods to determine if the phenotypic characteristics are stable.

To this end, the interspecific hybrids preferably originates from crossings between at least two of the following species: *Kalanchoe aromatica, Kalanchoe blossfeldiana, Kalanchoe campanulata, Kalanchoe crundallii, Kalanchoe gricilipes* and *Kalanchoe laciniata*.

Attractive examples of suitable interspecific hybrids between species within the genus *Kalanchoe* are e.g. *Kalanchoe* interspecific hybrids 'Adorable White Meadow', 'African Delight' (CVPO2012/0055), 'Fancy White Meadow', 'Delicate White Meadow', 'Sophisticated Pink Meadow', 'Amazing Pink Meadow' (CVPO 2011/1549), 'Adorable Pink Meadow' (CVPO 2013/2836), 'Blossom Pink Meadow', 'Beautiful Red Meadow', 'Fascinating Red Meadow', 'Juicy Pink Meadow', 'Tender White Meadow', 'Warm Orange Meadow', 'Romantic Pink Meadow', 'Romantic Orange Meadow', 'Feminine Pink Meadow (CVPO 2011/2696)', 'Feminine Orange Meadow', 'Spring Yellow, 'Warm Yellow Meadow (CVPO 2013/2835),', '2011-1274', Charming Purple Meadow'(CVPO 2013/2853), 'Surprising Desert' (CVPO 2013/0256), 'Shiny Red Meadow', 'Funky Red Meadow', 'Baroque Rose Meadow', 'Jazzy White Meadow', 'Loveable Pink Meadow' (CPVO 2014/1367), 'Shiny Coral', 'Smooth Yellow Meadow', 'Cheerful Orange Meadow', 'Dreaming Pink Meadow', 'Frozen White Meadow', 'Sugar Red', 'Tropical Parfait', '2005-0891', '2005-2693', '2011-5028', 2010-5011, 'Dreaming Pink', MADONNAQ2 (CVPO2013/1038), '2008-5200', '2012-5046', Yellow African', 2005-1333', 2009-5233', 5002-0127', '2004-4002', 2004-4012', '2008-5090', '2010-5110', 2010-5060', '2006-0013', '2011-1274' '2009-0938', '2009-0261', '2012-0939', '2009-1274', '2012-6026', '2011-0322' and 'Frozen White', in particular Fancy White Meadow, Delicate White Meadow, Blossom Pink Meadow, Beautiful Red Meadow, Amazing Pink Meadow, Adorable White Meadow, Adorable Pink Meadow, Fascinating Red Meadow, Juicy Pink Meadow, Lovable Pink Meadow, Sophisticated Pink Meadow, Tender White Meadow, Warm Yellow Meadow, Warm Orange Meadow, 2009-0938, 2009-0261, 2012-0939, 2009-1274, 2012-6026 and 2011-0322.

In particular, *Kalanchoe* interspecific hybrids 'Adorable White Meadow', 'Fancy White Meadow', 'Delicate White Meadow', 'Sophisticated Pink Meadow', 'Amazing Pink Meadow' (CVPO 2013/1549), 'Adorable Pink Meadow' (CVPO 2013/2836), 'Blossom Pink Meadow', ' Beautiful Red Meadow', 'Fascinating Red Meadow', 'Juicy Pink Meadow', 'Tender White Meadow', 'Warm Orange Meadow', 'Romantic Pink Meadow', 'Romantic Orange Meadow', 'Feminine Pink Meadow (CVPO 2011/2696)', 'Feminine Orange Meadow', 'Warm Yellow Meadow (CVPO 2013/2835), '2011-1274', 'Surprising Desert' (CVPO 2013/0256), 'Loveable Pink Meadow', 2009-0261, 2012-0939, 2009-1274, 2012-6026 and 2011-0322 provide for cut flowers having a stem length of at least 35 cm, 45 cm, 50 cm or more.

It has been shown that in addition to conferring longevity to other cut flowers, the flowers of the genus *Kalanchoe* have a very high longevity themselves, of up to at least 4 weeks, preferably 6-8 weeks in aqueous nutrient medium, whereas in the art *Kalanchoe* cut flowers are kept dry and start to wither and wilt after 2-3 weeks. As indicated, it was shown that when flowers of the genus *Kalanchoe* were kept in an aqueous nutrient medium such as tap water, optionally enriched with nutrients, it took longer for the said medium to foul.

Preferably, the one or more cut flowers to confer prolonged longevity to, belong to a genus different from *Kalanchoe*. Although it is possible for the one species of the genus *Kalanchoe* to prolong the longevity of other species of the *Kalanchoe* genus, the effect is more pronounced and significant when the first cut flowers belong to a different genus. E.g. *Kalanchoe* interspecific hybrids 'Adorable White Meadow', 'Fancy White Meadow', 'Delicate White Meadow', 'Sophisticated Pink Meadow', 'Amazing Pink Meadow' (CVPO 2013/1549), 'Adorable Pink Meadow' (CVPO 2013/2836), 'Blossom Pink Meadow', 'Beautiful Red Meadow', 'Fascinating Red Meadow', 'Juicy Pink Meadow', 'Tender White Meadow', 'Warm Orange Meadow', 'Romantic Pink Meadow', 'Romantic Orange Meadow', 'Feminine Pink Meadow (CVPO 2011/2696)', 'Feminine Orange Meadow', 'Warm Yellow Meadow (CVPO 2013/2835), '2011-1274', 'Surprising Desert' (CVPO 2013/0256), 'Loveable Pink Meadow', 2009-0938, 2009-0261, 2012-0939, 2009-1274, 2012-6026 and 2011-0322have been selected for their longevity and their ability to prolong longevity for cut flowers and decorative greenery of other species and varieties thereof belonging to the *Kalanchoe* genus but in particular to cut flowers and decorative greenery of a genus different from *Kalanchoe*.

In a very attractive embodiment, the bouquet comprises one or more cut flowers belonging to a genus different from *Kalanchoe*. Said flowers can be any cut flower, suitable to be held in an aqueous nutrient growth medium. Such cut flowers can e.g. be of the family of the Rosaceae, in particular of the genus *Rosa*, or of the genus *Chrysanthemum* (spray or disbud), *Tulipa, Lilium, Gerbera, Cymbidium, Freesia, Eustoma, Hydrangea, Hippeastrum, Alstromeria, Paeonia, Anthurium, Zanthedeschia, Dianthus, Gypsophila, Helianthus, Hypericum, Limonium, Hyacinthus, Ranunculus, Iris, Gladiolus, Solidago, Aster* and decorative greenery. It has been found that in the majority of cases, if not in all, the longevity is prolonged when the aqueous medium also contains, or contained, one or more cut flowers or decorative greenery belonging to the genus *Kalanchoe*. Therefore the term 'cut flower' also encompasses decorative greenery of which the stem is cut and being placed in contact with the aqueous nutrient medium. These are cut plants, incorporated in e.g. bouquets in particular for the green appearance and e.g. attractive leaf form, and to a much lesser extent for reason of their flowers, if present at all. Herein, however, such cut plants are deemed to be encompassed by the term 'cut flower', although it may be preferred for the majority of the cut flowers to indeed have attractive flowers instead or in addition thereto.

The said cut flower preferably comprises one or more cut flowers from the family of the Rosaceae, preferably from the genus *Rosa*, as it is shown that in particular the longevity of *Rosa* is significantly increase when a bouquet comprising *Rosa* also comprises *Kalanchoe*.

It has been found that only a few or even a single cut flower of the genus *Kalanchoe* is capable to confer prolonged longevity to a plurality of other cut flowers, in particular to plants of a different genus. So only the presence of a limited number of *Kalanchoe* flowers in the medium is necessary. So the florist is free to keep a bunch, i.e. a bouquet of cut flowers comprising many flowers not belonging to the genus *Kalanchoe*, in presence of only one or a few *Kalanchoe* flowers. However, it can be advantageous from an esthetic point of view to incorporate more flowers of the *Kalanchoe* genus in the bouquet. In an attractive embodiment, the one or more cut flowers in the bouquet belonging to a genus different from *Kalanchoe* comprise a plurality of cut flowers belonging to different genus, species and/or varieties, which is particularly attractive to the customer.

The invention also provides a method for conferring elongated freshness to an aqueous nutrient medium for cut flowers, comprising the step of contacting one or more cut flowers belonging to the genus *Kalanchoe* as defined above, with the cut surface of the stem thereof, with the aqueous nutrient medium.

Additionally, the invention further provides the use of one or more cut flowers belonging to the genus *Kalanchoe* as defined above for prolonging the longevity of one or more cut flowers belonging to a genus different from *Kalanchoe*.

It is also possible for the cut flowers of the genus *Kalanchoe* to be held in the aqueous medium before any other cut flowers, are put in the said aqueous medium. In that case, the said cut flower of the *Kalanchoe* genus should be kept in the said medium long enough to confer to the medium the quality needed to confer prolonged longevity to the other cut flowers envisaged to confer a prolonged longevity to. A period of at least one, but preferably some or more days such as 2, 3, 4, 5, 6 or 7 days is advisable. Such an approach would be advantageous for florists, who can pre-treat the aqueous medium intended to hold other cut flowers than of the *Kalanchoe* genus by allowing cut flowers of the genus *Kalanchoe* to enrich the said aqueous medium resulting in prolonged longevity of the cut flowers that are put in the said medium later, e.g. after the *Kalanchoe* flowers have been removed. These cut flowers will stand longer without withering, enabling the florist to offer the said flowers for sale for a longer period of time. However, the one or more cut flowers belonging to the genus *Kalanchoe* are preferably held in the aqueous medium simultaneously with the one or more other cut flowers, and are preferably part of the same bouquet as explained above. As discussed, the one or more cut flowers belonging to a genus different from *Kalanchoe* are preferably incorporated in a bouquet.

As it has now been found that cut flowers stay longer fresh when kept in an aqueous medium wherein one or more cut flowers of the genus *Kalanchoe* are kept or have been kept, the invention also relates to a method for conferring prolonged the longevity to one or more cut flowers belonging to a genus different from *Kalanchoe*, comprising the step of contacting the said one or more cut flowers together with one or more cut flowers belonging to the genus *Kalanchoe* as defined above, with the cut surface of the stem thereof, with an aqueous nutrient medium for the said cut flowers.

The invention is now further illustrated by the following figures and examples, wherein FIGS. 1A-G show different bouquets comprising both *Kalanchoe* and cut flowers, including greenery, of other species.

FIG. 2 shows *Kalanchoe* 'Spring Yellow Meadow' 3 weeks after harvest in top view (A) and in side view (B).

FIG. 3 shows the condition of cut flower *Kalanchoe* in combination with *Rosa* (left), *Rosa* ($2^{nd}$ from left), *Kalanchoe* ($3^{rd}$ from left), and water without plant (right) after 7 days in keeping quality room in accordance with example 2 from the side (3A), the top (3B) and in detail (3C). In the detail, the sample of *Rosa* alone is on the left and the sample of *Rosa* in combination with *Kalanchoe* is on the right.

FIG. 7 shows a bouquet containing *Kalanchoe* 'Adorable Pink Meadow', and the decorative greenery *Pistacia*, 3 weeks after harvesting of the cut flowers and decorative greenery, kept in tap water. FIG. 7A is a top view, whereas

EXAMPLE 1

Origin of Exemplified Varieties Suitable for Incorporation in a Bouquet

As a first step in making *Kalanchoe* hybrids, a *Kalanchoe* plant selection is crossed with a *Kalanchoe* selection from the same or another species or interspecific hybrid. Crossings are made by transferring pollen from pollen donor (♂) to pollen receiver (♀). After seed maturation and seed harvest, the seeds are germinated. After flower induction progeny are screened for e.g. plant height, branching habit, stem strength, flower size, flower color, petal number as well as ethylene sensitivity and flower longevity. Large numbers of progeny may have to be screened to identify hybrids that meet the trait requirements. The hybrid progeny plant with desirable phenotypic characteristics is propagated asexually by conventional methods to determine whether the phenotypic characteristics are stable.

Adorable Pink Meadow
Soft Pink double type (more than 35 petals) *Kalanchoe* interspecific (*laciniata*×*blossfeldiana*) hybrid.
Genetic background: crossing between
♀ y 2004-0916 (*Kalanchoe laciniata*×*blossfeldiana* hybrid)
♂ 1998-469 (*Kalanchoe laciniata*×*blossfeldiana* hybrid)
Adorable White Meadow
White double type (more than 35 petals) *Kalanchoe* interspecific (*laciniata*×*blossfeldiana*) hybrid.
White mutation found in Adorable Pink Meadow with the genetic background:
♀ 2004-0916 (*Kalanchoe laciniata*×*blossfeldiana* hybrid)
♂ 1998-469 (*Kalanchoe laciniata*×*blossfeldiana* hybrid)
Amazing Pink Meadow
Pink/soft orange double type (more than 35 petals) *Kalanchoe* interspecific (*laciniata*×*blossfeldiana*) hybrid.
Genetic background: crossing between
♀ 1998-469 (*Kalanchoe laciniata*×*blossfeldiana* hybrid)
♂ 2006-0199 (*Kalanchoe laciniata* hybrid)
Beautiful Red Meadow Red double type (more than 35 petals) *Kalanchoe* interspecific (*laciniata×lossfeldiana×gracilipes*) hybrid.
Genetic background: crossing between
♀ 2008-7042 (*Kalanchoe laciniata×gracilipes* hybrid)
♂ 2009-0517 (*Kalanchoe laciniata×blossfeldiana* hybrid)
Blossom Pink Meadow
Soft Pink double type (more than 35 petals) *Kalanchoe* interspecific (*laciniata×blossfeldiana×crundallii*) hybrid.
Genetic background: crossing between
♀ 2006-0547 (*Kalanchoe laciniata×blossfeldiana* hybrid)
♂ 0306 *Kalanchoe crundallii*
Delicate White Meadow
White double type *Kalanchoe* interspecific (*laciniata×aromatica*) hybrid.
Genetic background: crossing between
♀ 2003-0638 (*Kalanchoe laciniata* hybrid)
♂ 0091 B *Kalanchoe aromatica*
Fancy White Meadow
White double type *Kalanchoe* interspecific (*laciniata×crenata*) hybrid.
Genetic background: crossing between
♀ 2003-0818 (*Kalanchoe laciniata* hybrid)
♂ 0091B *Kalanchoe crenata*
Fascinating Red Meadow
Red double type *Kalanchoe* interspecific (*laciniata×blossfeldiana×gracilipes*) hybrid.
Genetic background: crossing between
♀ 2008-7042 (*Kalanchoe laciniata×gracilipes* hybrid)
♂ 2006-0645 (*Kalanchoe laciniata×blossfeldiana* hybrid)
Juicy Pink Meadow
Pink double type (more than 35 petals) *Kalanchoe* interspecific (*laciniata×blossfeldiana*) hybrid.
Genetic background: crossing between
♀ 2007-2024 (*Kalanchoe laciniata×blossfeldiana* hybrid)
♂ 2006-0199 (*Kalanchoe laciniata* hybrid)
Lovable Pink Meadow
Pink double type (more than 35 petals) *Kalanchoe* interspecific (*laciniata×blossfeldiana*) hybrid.
Genetic background: crossing between
♀ 1998-469 (*Kalanchoe laciniata×blossfeldiana* hybrid)
♂ 2006-0199 (*Kalanchoe laciniata* hybrid)
Sophisticated Pink Meadow
Pink double type *Kalanchoe* interspecific (*laciniata×blossfeldiana×campanulata*) hybrid.
Genetic background: crossing between
♀ 2003-0834 (*Kalanchoe laciniata×blossfeldiana* hybrid)
♂ 0098 *Kalanchoe campanulata*
Tender White Meadow
White double type (more than 35 petals) *Kalanchoe* interspecific (*laciniata×blossfeldiana*) hybrid.
Genetic background: crossing between
♀ 2005-0292 (*Kalanchoe laciniata×blossfeldiana* hybrid)
♂ 2003-1685 (*Kalanchoe laciniata×blossfeldiana* hybrid)
Warm Yellow Meadow
Yellow double type (more than 35 petals) *Kalanchoe* interspecific (*laciniata×blossfeldiana*) hybrid.
Genetic background: crossing between
♀ 2006-0199 (*Kalanchoe laciniata* hybrid)
♂ 2006-0473 (*Kalanchoe laciniata×blossfeldiana* hybrid)
Warm Orange Meadow
Orange double type (more than 35 petals) *Kalanchoe* interspecific (*laciniata×blossfeldiana*) hybrid.
Orange mutation found in Adorable Pink Meadow with the genetic background:
♀ 2006-0199 (*Kalanchoe laciniata* hybrid)
♂ 2006-0473 (*Kalanchoe laciniata×blossfeldiana* hybrid)
2009-0938
Greenish double type (more than 35 petals) *Kalanchoe* interspecific (*laciniata×blossfeldiana*) hybrid.
Genetic background: crossing between
♀ 2006-0846 (*Kalanchoe laciniata×blossfeldiana* hybrid)
♂ 2008-3894 (*Kalanchoe laciniata×blossfeldiana* hybrid)
2009-0261
White double type (more than 35 petals) *Kalanchoe* interspecific (*laciniata×blossfeldiana*) hybrid.
Genetic background: crossing between
♀ 2006-0199 (*Kalanchoe laciniata* hybrid)
♂ 2005-2519 (*Kalanchoe laciniata×blossfeldiana* hybrid)
2012-0939
Yellow double type (more than 35 petals) *Kalanchoe laciniata* hybrid.
Genetic background: crossing between
♀ 2006-0199 (*Kalanchoe laciniata* hybrid)
♂ 2006-0199 (*Kalanchoe laciniata* hybrid)
2009-1274
Yellow double type (more than 35 petals) *Kalanchoe laciniata* hybrid.
Genetic background: crossing between
♀ 2006-0199 (*Kalanchoe laciniata* hybrid)
♂ 2006-0199 (*Kalanchoe laciniata* hybrid)
2012-6026
Orange double type (more than 35 petals) *Kalanchoe* interspecific (*laciniata×blossfeldiana*) hybrid.
Genetic background: crossing between
♀ 2009-4162 (*Kalanchoe laciniata* hybrid)
♂ 2008-3870 (*Kalanchoe laciniata×blossfeldiana* hybrid)
2011-0322
Orange double type (more than 35 petals) *Kalanchoe* interspecific (*laciniata×blossfeldiana*) hybrid.
Genetic background: crossing between
♀ 2006-0199 (*Kalanchoe laciniata* hybrid)
♂ 2008-1089 (*Kalanchoe blossfeldiana* hybrid)

EXAMPLE 2

Viability of *Kalanchoe* in Aqueous Nutrient Medium

Figure 1A:
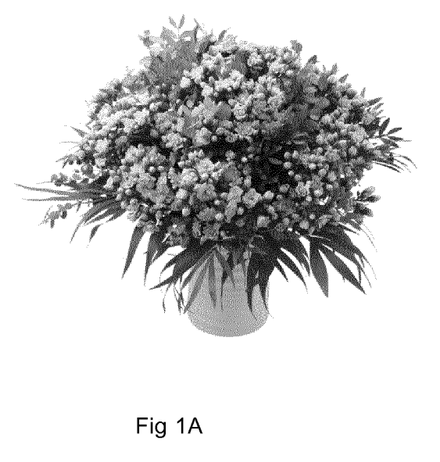
FIG. 1A shows a bouquet containing *Kalanchoe* 'Adorable Pink Meadow', and the following greenery: *Eucalyptus, Pistacia* and palm leaves.
Figure 1B:
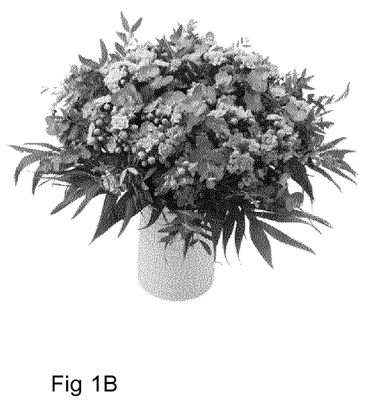
FIG. 1B shows a bouquet *Kalanchoe* 'Amazing Pink Meadow', and the following greenery: *Eucalyptus, Pistacia* and palm leaves.
Figure 1C:
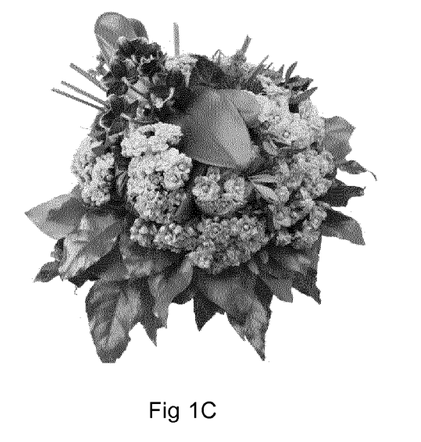
FIG. 1C shows a bouquet containing *Kalanchoe* 'Amazing Pink Meadow', *Phaelanopsis* and decorative greenery.
Figure 1D:
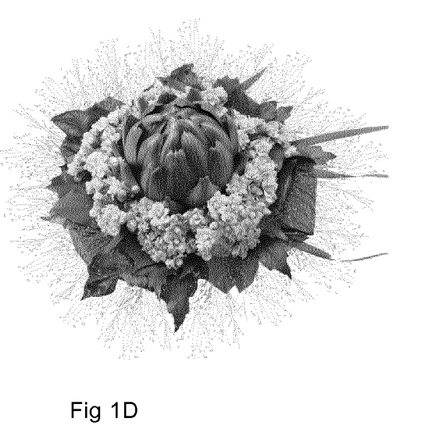
FIG. 1D shows a bouquet containing *Kalanchoe* 'Adorable Pink Meadow', *Cynara* and decorative greenery.
Figure 1E:
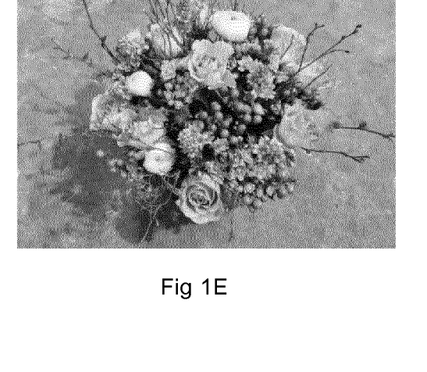
FIG. 1E shows a bouquet containing *Kalanchoe* 'Amazing Pink Meadow', *Rosa, Hyacinthus, Hypericon, Ranunculus* and decorative greenery.
Figure 1F:
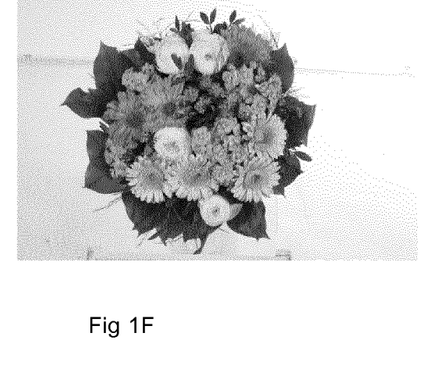
FIG. 1F shows a bouquet containing *Kalanchoe* 'Amazing Pink Meadow', *Rosa, Hyacinthus, Gerbera, Ranunculus* and decorative greenery.
Figure 1G:
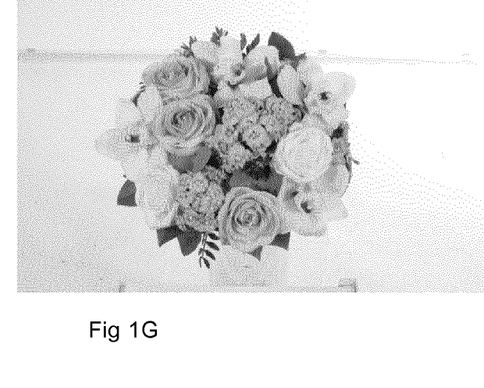
FIG. 1G shows a bouquet containing *Kalanchoe* 'Amazing Pink Meadow', *Rosa, Cymbidium* and decorative greenery.
Figure 2A:
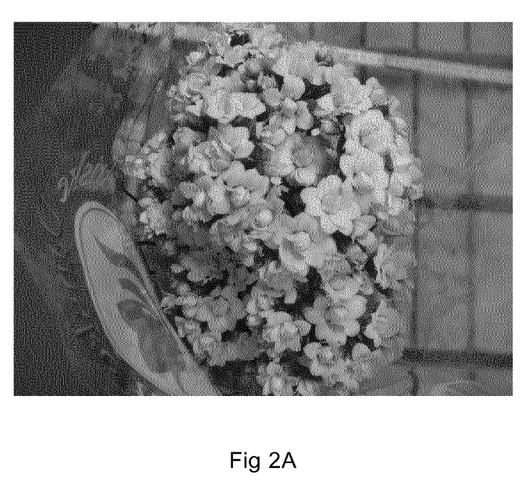
Figure 2B:
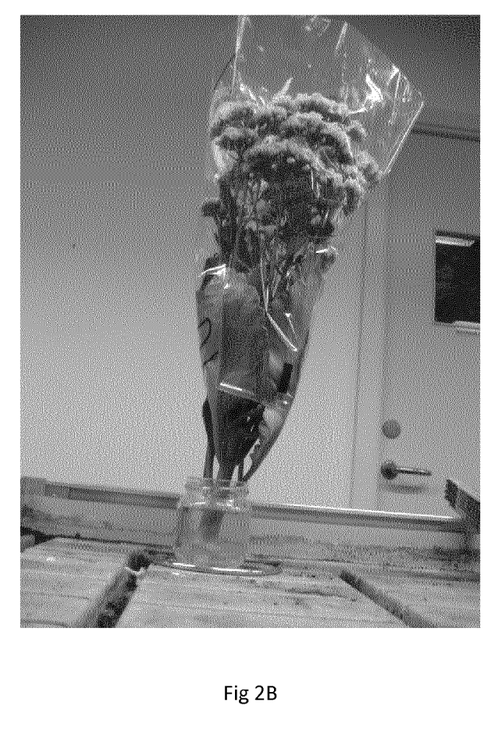
Figure 3A:
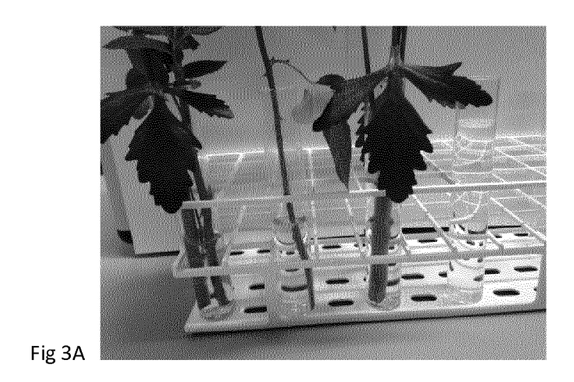
Figure 3B:
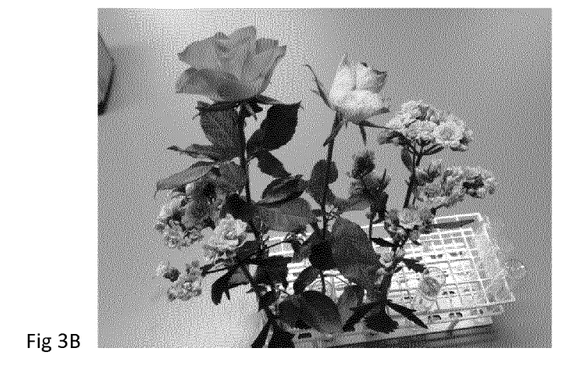
Figure 3C:
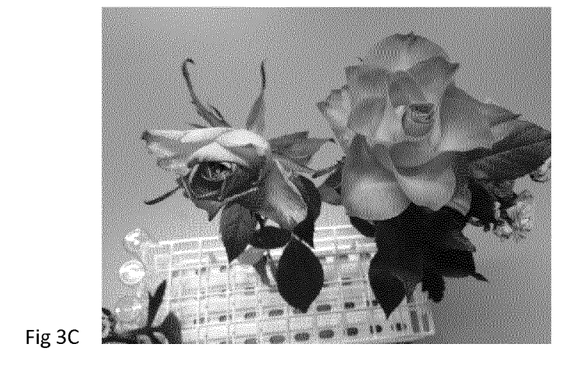
Figure 4:
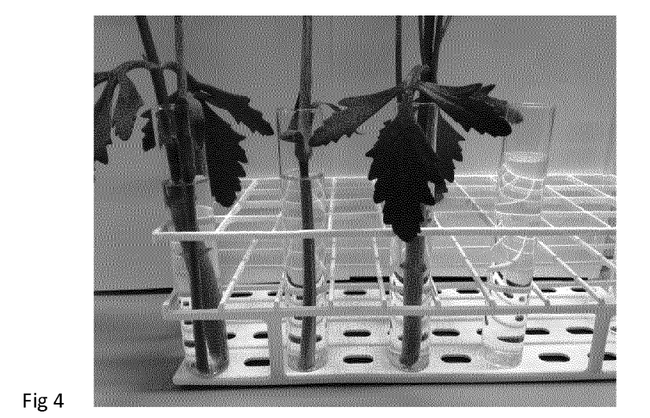
FIG. 4 shows the condition of cut flower *Kalanchoe* in combination with *Dianthus* (left), *Dianthus* ($2^{nd}$ from left), *Kalanchoe* ($3^{rd}$ from left), and water without plant (right) after 7 days in keeping quality room in accordance with example 2 from the side.
Figure 5:
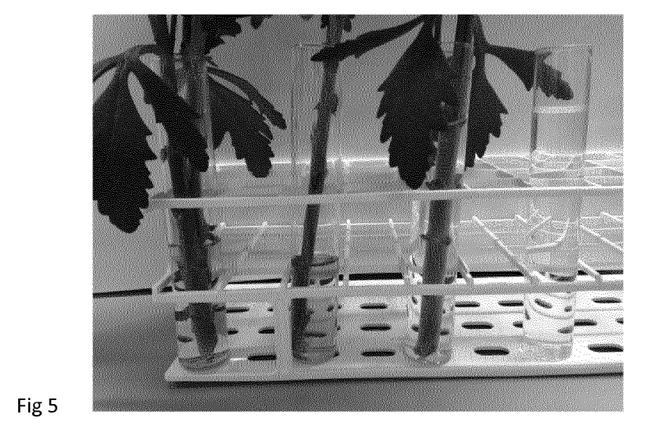
FIG. 5 shows the condition of cut flower *Kalanchoe* in combination with *Chrysanthemum* (left), *Chrysanthemum* ($2^{nd}$ from left), *Kalanchoe* ($3^{rd}$ from left), and water without plant (right) after 7 days in keeping quality room in accordance with example 2 from the side.
Figure 6:
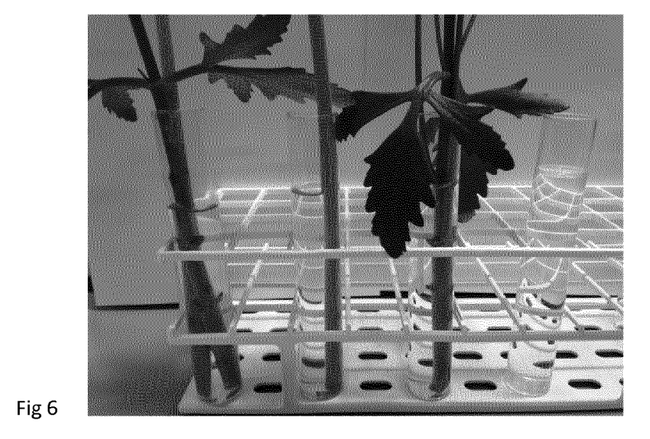
FIG. 6 shows the condition of cut flower *Kalanchoe* in combination with *Gerbera* (left), *Gerbera* ($2^{nd}$ from left), *Kalanchoe* ($3^{rd}$ from left), and water without plant (right) after 7 days in keeping quality room in accordance with example 2 from the side.

Different *Kalanchoe* varieties were harvested by cutting their stems, wrapped in plastic, placed in transport card board boxes, and stored for 5 days in darkness at 18° C. to mimic transport. The plants were placed in keeping quality room (Temperature: 19° C., Light: 8 h/day, Light intensity: 10 µmol/m²/s), the cut stem of the cut flower being submerged in tap water. Evaluation of the cut flower plant height, fading, wilting, stem strength, and ornamental value took place 3 weeks after harvest. Just before the evaluation, the tested varieties were photographed from the top and the side, see FIGS. 2A and 2B, respectively.

As shown in table 1, wherein data concerning plant height (cm), fading (1-5, 1=no fading), wilting (1-5, 1=no wilting), stem strength (1-5, 1=very strong), ornamental value (1-5, 1=highest ornamental value), were measured 3 weeks after excision of the flower stems at the basal part of the *Kalanchoe* plant. At harvest, the values were '1'.

It can be seen that all varieties keep their qualities after being kept in tap water. The tap water remained clear during this period and even longer, see also FIG. 2B.

TABLE 1

Quality of different *Kalanchoe* varieties after being kept for 3 weeks in tap water

| Variety | Height | Fading | Wilting | Stem strength | Ornamental value |
|---|---|---|---|---|---|
| 2010-7367 | 40 | 2 | 1 | 2 | 2 |
| Warm Yellow | 40 | 3 | 2 | 1 | 2 |
| 2011-0036 | 34 | 3 | 2 | 2 | 3 |
| Spring Yellow Meadow | 42 | 1 | 1 | 1 | 1 |
| 2009-0377 | 43 | 2 | 2 | 2 | 2 |
| 2009-0938 | 32 | 1 | 1 | 1 | 1 |
| 2010-2541 | 35 | 2 | 1 | 1 | 2 |
| 2010-7027 | 45 | 2 | 3 | 1 | 3 |
| 2010-0209 | 36 | 2 | 2 | 2 | 2 |
| 2008-4048 | 37 | 2 | 2 | 1 | 2 |
| MADONNAQ2 | 35 | 1 | 1 | 1 | 1 |
| Amazing Pink Meadow | 54 | 2 | 1 | 1 | 1 |
| Dreaming Pink | 42 | 1 | 2 | 1 | 1 |
| Adorable Pink Meadow | 43 | 1 | 1 | 1 | 1 |
| Lovable Pink Meadow | 41 | 1 | 1 | 2 | 1 |
| 2009-0192 | 39 | 1 | 1 | 1 | 1 |
| 2009-1161 | 35 | 1 | 1 | 2 | 1 |
| 2008-6037 | 42 | 2 | 2 | 1 | 2 |
| Vintage Pink Meadow | 44 | 1 | 2 | 1 | 1 |
| 2010-0792 | 44 | 1 | 2 | 1 | 1 |
| 2009-0701 | 36 | 1 | 3 | 1 | 2 |
| 2011-2200 | 39 | 1 | 1 | 1 | 1 |
| 2011-2187 | 43 | 1 | 1 | 1 | 1 |
| 2010-7099 | 46 | 1 | 1 | 2 | 1 |
| 2010-6038 | 35 | 2 | 1 | 3 | 2 |
| 2010-6013 | 35 | 1 | 1 | 3 | 2 |
| 2010-7018 | 42 | 1 | 3 | 1 | 3 |
| 2009-0219 | 36 | 1 | 1 | 1 | 1 |
| 2010-6031 | 35 | 2 | 1 | 2 | 2 |

EXAMPLE 3

Effect of *Kalanchoe* on Freshness of Nutrient Medium and Longevity of Other Cut Flowers—Single Flower Test Cut flowers *Rosa*, *Dianthus*, *Chrysanthemum* and *Gerbera*, alone or together with a cut flower of *Kalanchoe* 'Amazing Pink Meadow' were kept for 7 days in keeping quality room (Temperature: 19° C., Light: 8 h/day, Light intensity: 10 μmol/m²/s) in 28.5 ml tap water (pH 6.8, EC 0.72 mS/cm), 1 flower stem per cylinder glass for the test of individual species or together with a *Kalanchoe* flower stem. Water consumption was measured. Light transmission was measured in samples of 5 ml of the tap water of the flowers and compared to tap water stored in similar vial under same conditions for 7 days. This was done at 340nm using a Spectroquant SC118, Merck, (Method 242).

Seven days after start of the experiment the plants were evaluated for fading (1-5, 1=no fading), wilting (1-5, 1=no wilting), ornamental value (1-5, 1=highest ornamental value), and water consumption (ml), see table 2. At the start of the experiment, the values for fading, wilting and ornamental value were set to 1.

On the fading evaluation, there was a slight positive effect of combining *Rosa* with *Kalanchoe* (1.3 vs. 2). The same is true for *Dianthus* (1.4 vs. 1.5). In *Chrysanthemum* and *Gerbera* no effect was found after 7 days.

In *Rosa* there was a positive effect of combining *Rosa* with *Kalanchoe* on the wilting evaluation (2 vs. 4).

The ornamental value of all species tested was improved by combining *Rosa* with *Kalanchoe* (2 vs. 4) and *Dianthus* with *Kalanchoe* (1.3 vs. 1.7) and *Chrysanthemum* with *Kalanchoe* (1.5 vs. 2.2) and *Gerbera* with *Kalanchoe* (1.1 vs. 1.5).

Water consumption was calculated by subtracting the amount of water 7 days after start of the experiment from the initial amount of water at the start of the experiment. Of the 5 species tested, *Kalanchoe* had the significantly lowest water consumption. For *Kalanchoe* combined with *Rosa* the uptake of water (16.6 ml) was higher that when adding the individual uptake from *Kalanchoe* (3.4 ml) with the individual uptake from *Rosa* (11.6 ml). An obvious explanation is that the individual *Rosa* started wilting relative early compared to the *Rosa* combined with *Kalanchoe*. The same pattern is seen in *Gerbera*. For *Kalanchoe* combined with *Gerbera* the uptake of water (11.9 ml) was higher that when adding the individual uptake from *Kalanchoe* (3.4 ml) with the individual uptake from *Gerbera* (6.3 ml).

TABLE 2

Effect of *Kalanchoe* on longevity and medium freshness

| | Fading | | Wilting | | Ornamental value | | Water consumption | | Transmission | |
|---|---|---|---|---|---|---|---|---|---|---|
| | | * | | * | | * | average (n = 4) | s.e. (n = 4) | average (n = 4) | s.e. (n = 4) |
| *Kalanchoe* 'Amazing Pink Meadow' | 1.3 | — | 1 | — | 1.1 | — | 3.4 | 0.0 | 98.1 | 2.8 |
| Roses | — | 2 | — | 4 | — | 4 | 11.6 | 0.6 | 58.7 | 3.4 |
| *Kalanchoe* and Roses* | 1.3 | 1.3 | 1 | 2 | 1.1 | 2 | 16.6 | 0.2 | 93.4 | 1.3 |
| *Dianthus* | — | 1.5 | — | 1 | — | 1.7 | 6.3 | 0.1 | 86.9 | 4.1 |
| *Kalanchoe* and *Dianthus** | 1.3 | 1.4 | 1 | 1 | 1.1 | 1.3 | 9.2 | 0.1 | 95.8 | 0.6 |
| *Chrysanthemum* | — | 1.2 | — | 1 | — | 2.2 | 15.0 | 0.1 | 15.7 | 3.8 |
| *Kalanchoe* and *Chrysanthemum** | 1.3 | 1.2 | 1 | 1 | 1.1 | 1.5 | 18.5 | 0.1 | 35.8 | 8.8 |
| *Gerbera* | — | 1 | — | 1 | — | 1.5 | 6.3 | 0.1 | 64.9 | 0.3 |
| *Kalanchoe* and *Gerbera** | 1.3 | 1 | 1 | 1 | 1.1 | 1.1 | 11.9 | 0.1 | 72.0 | 1.9 |
| Water | — | — | — | — | — | — | 1.4 | 0.0 | 97.8 | 0.9 |
| Water (start) | — | — | — | — | — | — | 0 | 0 | 100 | 0 |

In *Gerbera* we experience higher water uptake in combination with *Kalanchoe*, although no wilting after 7 days (as for *Rosa*), but we can see that light transmission was higher through water from *Kalanchoe* combined with *Gerbera*, than from individual *Gerbera*. We see clear effects of increased light transmission through the water for all four species when combined with *Kalanchoe*, supporting the idea that cut flowers of the genus *Kalanchoe* comprise one or more substances that are excreted in the aqueous nutrient medium, or that substances excreted from plants of other species are taken up by *Kalanchoe* or that the excreted substances for the other species are eliminated or degraded by substances excreted from *Kalanchoe*. As a result of these plants of species other than *Kalanchoe* obtain the ability to live longer and to wither far later than compared to the situation without a cut flower of the genus *Kalanchoe* being, or having been in contact with the aqueous nutrient medium wherein the said cut flower is held. See also FIGS. 3-6. Similar results were obtained when any of the *Kalanchoe* varieties as mentioned in example 1 were used instead of the *Kalanchoe* variety 'Amazing Pink Meadow' as described here.

EXAMPLE 4

Figure 7A:
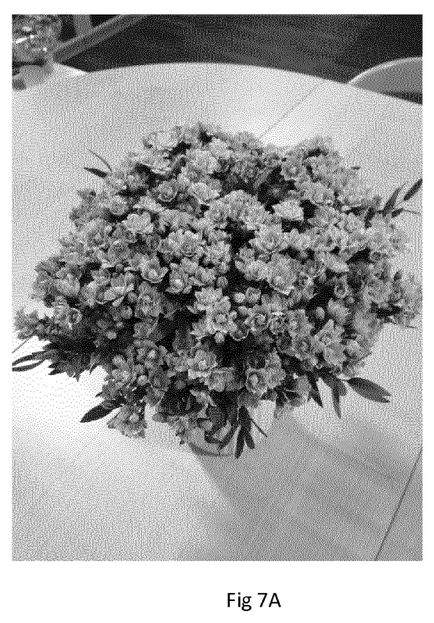
Figure 7B:
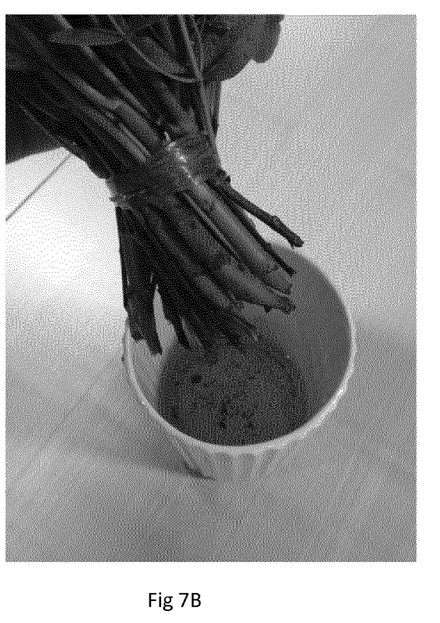
FIG. 7B shows the stems of same bouquet.
Figure 7C:
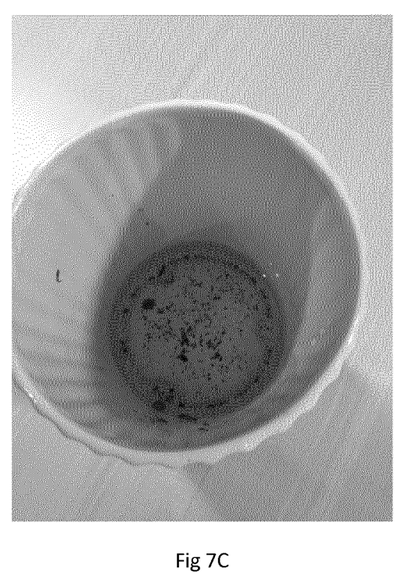
FIG. 7C is a close up of the tap water after 3 weeks.

Effect of *Kalanchoe* on Freshness of Nutrient Medium and Longevity of Other Cut Flowers—Bouquet Test A bouquet containing the *Kalanchoe* interspecific hybrid 'Adorable Pink Meadow', and the decorative greenery *Pistacia* was kept in a quality room (Temperature: 19° C., Light: 8 h/day, Light intensity: 10 $\mu$mol/m$^2$/s) in tap water (pH 6.8, EC 0.72 mS/cm) for 3 weeks after harvesting of the cut flowers and decorative greenery. Both the cut flowers and decorative greenery remained fresh, as well as the basal parts of both. See FIGS. 7A and 7B, respectively. The tap water remained fresh during this period, see FIG. 7C. The amount of water was reduced by 75% over the 3 weeks indicating significant uptake of water and compounds emitted from the *Kalanchoe* cut flowers. The transmission through the water that has surrounded the basal parts of the cut flowers and decorative greenery was measured. We found the transmission to be reduced to 91.7% of the initial 100% measured in tap water. The very high transmission rate and the lack of any odors from the water indicate that there are no significant microbial activity in the water. Similar results were obtained for other *Kalanchoe* containing bouquets, such as shown in FIGS. 1A-G.

EXAMPLE 5

*Kalanchoe* Live Longer in Tap Water than Without

Figure 8A:
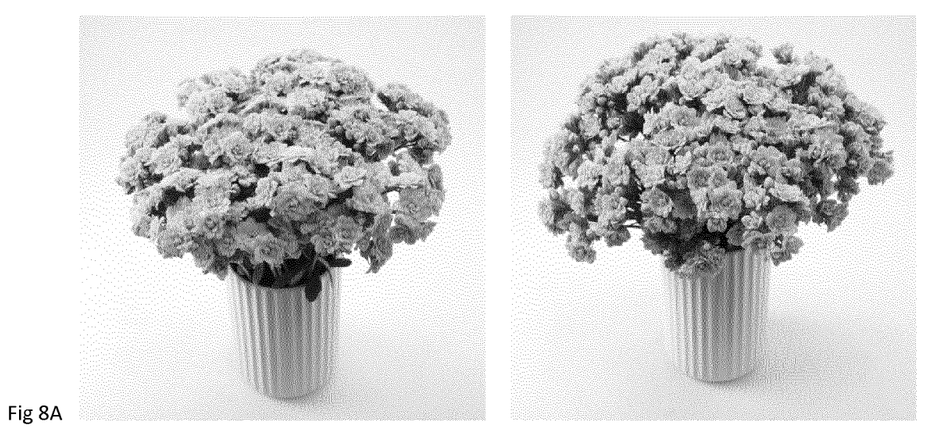
FIGS. 8A-C show bouquets containing *Kalanchoe* 'Amazing Pink Meadow' kept for over 5 weeks in a quality room (Temperature: 19° C., Light: 8 h/day, Light intensity: 10 µmol/m$^2$/s) in tap water (pH 6.8, EC 0.72 mS/cm) (left panel) or without water (right panel) after 1 (A), 2 (B), and 5 (C) weeks after harvest.
Figure 8B:
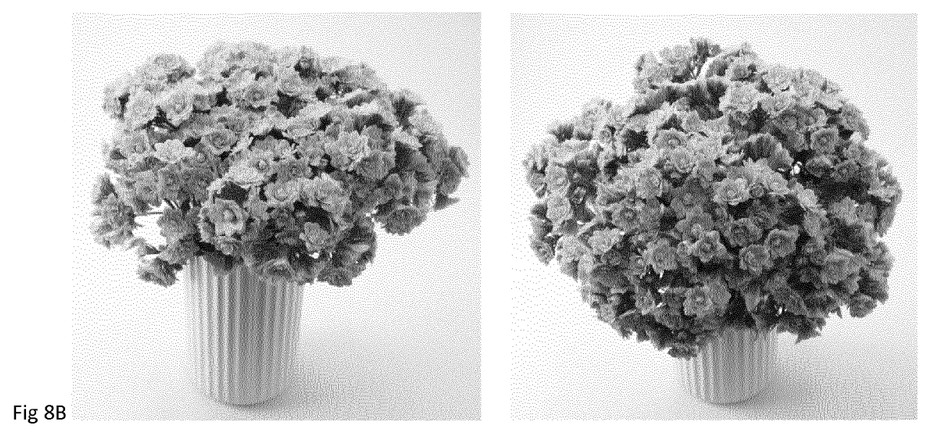
Figure 8C:
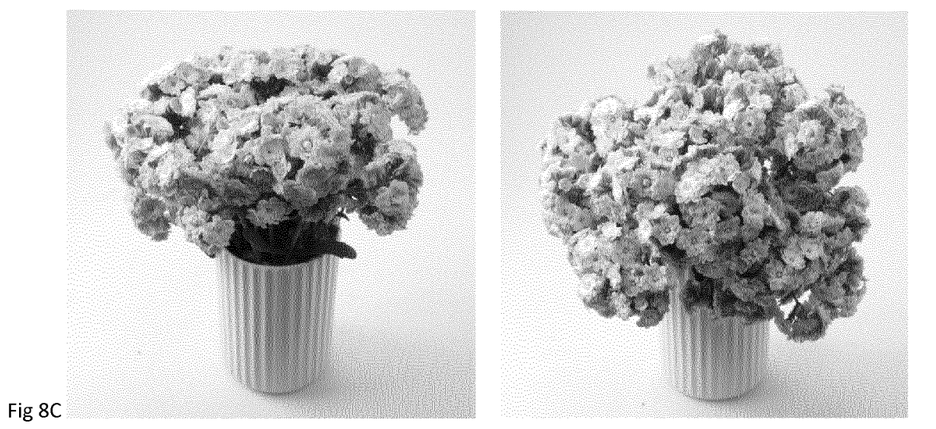

A bouquet containing *Kalanchoe* 'Amazing Pink Meadow' was kept for over 5 weeks in a quality room (Temperature: 19° C., Light: 8 h/day, Light intensity: 10 $\mu$mol/m$^2$/s) in tap water (pH 6.8, EC 0.72 mS/cm) or without. After 1, 3 and 5 weeks, the flowers were evaluated and it was shown that the flowers that were kept in tap water kept more fresh than those without water. See FIGS. 8A-C, respectively.

The invention claimed is:

1. A bouquet of cut flowers, comprising:
    a container of an aqueous nutrient medium for cut flowers;
    one or more cut flowers from a plant that is an interspecific hybrid of species belonging to the genus *Kalanchoe*, said interspecific hybrid originating from a crossing with *Kalanchoe blossfeldiana*, said flowers having a stem length of at least 35 cm, the cut surface of the stems of said cut flowers being submerged in said aqueous nutrient medium, wherein said flowers confer elongated freshness to said aqueous nutrient medium by contact of the submerged cut surface of the stems of the said cut flowers with said aqueous nutrient medium; and
    one or more cut flowers belonging to a genus different from *Kalanchoe*, the cut surface of the stems thereof being submerged in said aqueous nutrient medium, wherein said cut flowers belonging to a genus different from *Kalanchoe* have prolonged longevity by contact of the submerged cut surface of the stems thereof with said aqueous nutrient medium.

2. The bouquet of claim 1, wherein the cut flowers from a plant that is an interspecific hybrid of species belonging to the genus *Kalanchoe* have a stem length of at least 45 cm.

3. The bouquet of claim 1, wherein the cut flowers from a plant that is an interspecific hybrid of species belonging to the genus *Kalanchoe* have a stem length of 60 cm or more.

4. The bouquet of claim 1, wherein the cut flowers from a plant that is an interspecific hybrid of species belonging to the genus *Kalanchoe* are free of branches that originate from the lower third of the stem of the cut flower.

5. The bouquet of claim 1, wherein the cut flowers from a plant that is an interspecific hybrid of species belonging to the genus *Kalanchoe* are free of branches that originate from the lower half of the stem of the cut flower.

6. The bouquet of claim 1, wherein the cut flowers from a plant that is an interspecific hybrid of species belonging to the genus *Kalanchoe* are free of branches that do not reach the upper third of the stem.

7. The bouquet of claim 6, wherein the cut flowers from a plant that is an interspecific hybrid of species belonging to the genus *Kalanchoe* are free of branches that do not reach the upper quarter of the stem.

8. The bouquet of claim 1, wherein the plant that is an interspecific hybrid of species belonging to the genus *Kalanchoe* originates from crossings between *Kalanchoe blossfeldiana* and one at least one of the following species: *Kalanchoe aromatica*, *Kalanchoe campanulata*, *Kalanchoe crundallii*, *Kalanchoe gricilipes* and *Kalanchoe laciniata*.

9. The bouquet of claim 1, further including one or more additional cut flowers belonging to a genus, species and/or variety different from the other cut flowers.

10. The bouquet of claim 1, wherein the cut flowers from a plant that is an interspecific hybrid of species belonging to the genus *Kalanchoe* are of the double type.

11. The bouquet of claim 1, wherein the cut flowers from a plant that is an interspecific hybrid of species belonging to the genus *Kalanchoe* are free of branches that originate from the lower quarter of the stem of the cut flower.

12. The bouquet of claim 11, wherein the cut flowers from a plant that is an interspecific hybrid of species belonging to the genus *Kalanchoe* have not been subjected to removal of branches.

13. The bouquet of claim 1, wherein the plant that is an interspecific hybrid of species belonging to the genus *Kalanchoe* originates from a crossing between *Kalanchoe laciniata* and *Kalanchoe blossfeldiana*.

14. The bouquet of claim 13, wherein said cut flowers belonging to a genus different from *Kalanchoe* are cut flowers from the family Rosaceae.

15. The bouquet of claim 13, wherein said cut flowers belonging to a genus different from *Kalanchoe* are cut flowers from the genus *Rosa*.

16. A method for conferring elongated freshness to an aqueous nutrient medium for cut flowers, comprising submerging the cut ends of one or more cut flowers from a plant that is an interspecific hybrid of species belonging to the genus *Kalanchoe*, said flower having a stem length of at least 35 cm, in the aqueous nutrient medium, wherein the plant that is an interspecific hybrid of species belonging to the genus *Kalanchoe* originates from a crossing with *Kalanchoe blossfeldiana*.

17. The method of claim 16, wherein the cut ends of one or more cut flowers belonging to a genus different from *Kalanchoe* are also submerged in the same aqueous nutrient medium.

18. The method of claim 16, wherein the cut flowers from a plant that is an interspecific hybrid of species belonging to the genus *Kalanchoe* are free of branches that originate from the lower quarter of the stem of the cut flower.

19. The bouquet of claim 16, wherein the plant that is an interspecific hybrid of species belonging to the genus *Kalanchoe* originates from a crossing between *Kalanchoe laciniata* and *Kalanchoe blossfeldiana*.

20. A method for conferring prolonged longevity to one or more cut flowers belonging to a genus different from *Kalanchoe*, comprising submerging the cut ends of the said one or more cut flowers belonging to a genus different from *Kalanchoe* together with the cut ends of one or more cut flowers from a plant that is an interspecific hybrid of species belonging to the genus *Kalanchoe*, said flowers having a stem length of at least 35 cm, in said aqueous nutrient medium, wherein the plant that is an interspecific hybrid of species belonging to the genus *Kalanchoe* originates from a crossing with *Kalanchoe blossfeldiana*.

21. The method of claim 20, wherein the cut flowers from a plant that is an interspecific hybrid of species belonging to the genus *Kalanchoe* are free of branches that originate from the lower quarter of the stem of the cut flower.

22. The method of claim 20, wherein the plant that is an interspecific hybrid of species belonging to the genus *Kalanchoe* originates from a crossing between *Kalanchoe laciniata* and *Kalanchoe blossfeldiana*.

23. A bouquet of cut flowers intended to have the cut ends thereof submerged in aqueous nutrient medium for display, comprising:
one or more cut flowers from a plant that is an interspecific hybrid of species belonging to the genus *Kalanchoe*, said flowers having a stem length of at least 35 cm, wherein the plant that is an interspecific hybrid of species belonging to the genus *Kalanchoe* originates from a crossing with *Kalanchoe blossfeldiana*; and
one or more cut flowers belonging to a genus different from *Kalanchoe*,
wherein said flowers are held together by a foil wrap or a binder that hold the stems of the flowers together until the foil wrap or binder is removed and the cut ends of the flowers placed in an aqueous nutrient medium.

24. The bouquet of claim 23, wherein the cut flowers from a plant that is an interspecific hybrid of species belonging to the genus *Kalanchoe* are free of branches that originate from the lower quarter of the stem of the cut flower.

25. The method of claim 23, wherein the plant that is an interspecific hybrid of species belonging to the genus *Kalanchoe* originates from a crossing between *Kalanchoe laciniata* and *Kalanchoe blossfeldiana*.

* * * * *

UNITED STATES PATENT AND TRADEMARK OFFICE
CERTIFICATE OF CORRECTION

PATENT NO. : 10,932,426 B2
APPLICATION NO. : 15/114281
DATED : March 2, 2021
INVENTOR(S) : Christensen et al.

Page 1 of 1

It is certified that error appears in the above-identified patent and that said Letters Patent is hereby corrected as shown below:

In the Claims

At Claim 19, Column 15, Line 22, delete "The bouquet of claim 16," and insert --The method of claim 16,--.

At Claim 25, Column 16, Line 29, delete "The method of claim 23," and insert --The bouquet of claim 23,--.

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*